US00PP27467P3

(12) United States Plant Patent
Bradford

(10) Patent No.: US PP27,467 P3
(45) Date of Patent: Dec. 20, 2016

(54) PEACH TREE NAMED 'PEARL PRINCESS IV'

(50) Latin Name: *Prunus persica*
Varietal Denomination: Pearl Princess IV

(71) Applicant: Lowell Glen Bradford, Le Grand, CA (US)

(72) Inventor: Lowell Glen Bradford, Le Grand, CA (US)

( * ) Notice: Subject to any disclaimer, the term of this patent is extended or adjusted under 35 U.S.C. 154(b) by 77 days.

(21) Appl. No.: 14/544,246

(22) Filed: Dec. 15, 2014

(65) Prior Publication Data

US 2016/0174439 P1 Jun. 16, 2016

(51) Int. Cl.
*A01H 5/08* (2006.01)

(52) U.S. Cl.
USPC ..... Plt./196

(58) Field of Classification Search
USPC ..... Plt./196
See application file for complete search history.

(56) References Cited

U.S. PATENT DOCUMENTS

PP12,570 P2 4/2002 Bradford
PP19,919 P2 4/2009 Bradford

*Primary Examiner* — Anne Grunberg

(57) ABSTRACT

The present invention relates to a new and distinct variety of peach tree, *Prunus persica*, broadly characterized by a medium size, vigorous, hardy, self-fertile, productive and regular bearing tree. The variety blooms during the early to mid season and requires about 450 chilling hours. The fruit matures under the ecological conditions described in the latter part of June, with first picking on Jun. 20, 2014. The fruit is uniform, large in size, globose to oblate in shape, freestone in type, firm in texture, pinkish white in flesh color, full red in skin color, and a tasty balance of light acid and sugar in flavor.

1 Drawing Sheet

Botanical classification: *Prunus persica.*
Variety denomination: 'PEARL PRINCESS IV'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of peach tree, which has been denominated varietally as 'Pearl Princess IV'.

The present variety was hybridized by me in 2000 as a first generation cross using 'Snow Princess' (U.S. Plant Pat. No. 12,570) peach as the selected seed parent and an unnamed yellow flesh nectarine (unpatented) as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2006 I selected the present variety as a single tree from the group of seedlings described above. Subsequent to origination of the present variety of peach tree, I asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its seed parent 'Snow Princess' (U.S. Plant Pat. No. 12,570) peach, by having a vigorous tree, by having large blossoms that bloom in the early to mid season, by having reniform leaf glands, by being self-fertile, and by producing white flesh freestone peaches that are large in size, mostly red in skin color, globose in shape, very good in flavor, and firm in texture, but is distinguished therefrom by producing fruit that matures about thirty days earlier and that has a flavor that is a balance between light acid and sugar, rather than sub-acidic.

The present variety is very distinguished from its pollen parent by producing fruit that is peach instead of nectarine, that is white flesh instead of yellow flesh, and that is freestone instead of clingstone.

The present variety is most similar to 'Pearl Princess V' (U.S. Plant Pat. No. 19,919) peach, by having a vigorous tree with large blossoms and reniform leaf glands, being self-fertile, and producing white flesh freestone peaches that are mostly red in skin color, globose to oblate in shape, firm in texture, and very good in flavor, but is distinguished therefrom by producing fruit that matures about seven days later and is somewhat larger in size.

SUMMARY OF VARIETY

In summary, the present peach variety is characterized by a medium size, vigorous, hardy, self-fertile, productive and regular bearing tree. The variety blooms during the early to mid season and requires about 450 chilling hours. The fruit matures under the ecological conditions described in the latter part of June, with first picking on Jun. 20, 2014. The fruit is uniform, large in size, globose to oblate in shape, freestone in type, firm in texture, pinkish white in flesh color, full red in skin color, and a tasty balance of light acid and sugar in flavor.

DRAWING

The accompanying photograph consists of four whole fruits positioned to display the characteristics of the skin color and form, one divided fruit to reveal the flesh and stone, two insets to reveal buds and blossoms, a typical tip shoot and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 24, 2014, on a multiplied tree during its seventh growing season. The blossom and flower descriptions were made the previous blooming season. All major color code designations are by reference to the Inter-Society Color Council, National Bureau of Standards. Common color names are also used occasionally.

It is to be noted that 2014 was an abnormal year with drought conditions existing in California. The unusually clear, warm, and dry weather in January led to a very low amount of acquired chilling units, an earlier than normal blooming season, and an earlier than normal ripening season for the entire spring and summer.

PARENTAGE

Seed parent: 'Snow Princess' (U.S. Plant Pat. No. 12,570) peach.

Pollen parent: Unnamed nectarine (unpatented).

TREE

Size: Medium, reaching and maintaining a height of 10' [3.05 m.] and a spread of 9' [2.74 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 450 hours.

Trunk:

*Size*.—Medium, reaching a maximum diameter of 5" [127 mm.] after the seventh growing season.

*Texture*.—Shaggy.

*Bark color*.—Dark yellowish brown [78. d.yBr] with Moderate brown [58. m.Br] crevices present.

*Lenticels*.—Approximate Number Per Square Inch: 8. Color: Moderate orange [53. m.O]. Size: ¼" [6.4 mm.] to ½" [12.7 mm.] in length. Width is typically one fourth as much as the length. Shape: Eye-shaped, elongated.

Branches:

*Size*.—Medium, diameter of main scaffold is 3" [76.2 mm.] measured 12" above the crotch, diameter of limb is 1¾" [44.5 mm.] measured 12" above the first fork.

*Texture*.—Medium, shaggy.

*Color*.—1st Year Wood Topside: Grayish red [19. gy.R]. 1st Year Wood Underside: Brilliant yellow green [116. brill.YG]. 2nd Year and Older Wood: Deep yellowish brown [75. deep yBr].

*Lenticels*.—Number Per Square Inch: About 90 on second year wood. Color: Moderate orange yellow [71. m.OY]. Size: Small, 1/64" [0.4 mm.] to ⅛" [3.2 mm.] in length on second year wood. Width is typically one fourth as much as the length. Shape: Rectangular, elongated.

Leaves:

*Size*.—Medium. Average Length: 5¼" [133 mm.]. Average Width: 1½" [38 mm.].

*Arrangement*.—Alternate.

*Thickness*.—Medium.

*Form*.—Elliptical.

*Apex*.—Acuminate.

*Base*.—Rounded to slightly acute.

*Surface*.—Smooth.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Vein color*.—Pale yellow green [121. p.YG].

*Petiole*.—Average Length: ⅜" [9.5 mm.]. Average Thickness: 1/16" [1.6 mm.]. Color: Brilliant yellow green [116. brill.YG].

*Stipules*.—Number: Typically 2 per leaf at development stage. Average Length: ¼" [6.4 mm.]. Color: Deep yellow green [118. deep YG] becoming Dark olive green [126. d.OlG] with maturity.

*Glands*.—Number: 2 to 4 per leaf. Position: Oppositely positioned on the petiole, with the glands having a slight offset but not alternate. Size: Medium, about 1/24" [1.1 mm.] in length. Form: Reniform. Color: Deep yellow green [118. deep YG] becoming Moderate brown [58. m.Br] with age.

*Leaf buds*.—Pointed, medium in size.

Flower buds:

*Hardiness*.—Hardy, with respect to central California winters.

*Diameter*.—Typically ⅜" [9.5 mm.] 1 week before bloom.

*Length*.—Typically ⅝" [15.9 mm.] 1 week before bloom.

*Form*.—Not appressed.

*Surface*.—Pubescent.

*Tip color*.—Light purplish pink [249. l.pPk].

Flowers: Perfect, complete, perigynous, usually a single pistil, about thirty stamens, five sepal and petal locations alternately positioned.

*Type*.—Showy, medium to large.
*Average flower diameter*.—1¾" [44.5 mm.].
*Average flower depth*.—7/16" [11.1 mm.] when fully open.
*Number of petals*.—Five, extra petal fragments are observed on about ten percent, double blossoms not observed.
*Petal shape*.—Circular to oval.
*Petal margin*.—Entire, wavy.
*Average petal diameter*.—¾" [19.1 mm.].
*Average petal length*.—¾" [19.1 mm.].
*Petal apex*.—Rounded.
*Petal base*.—Rounded.
*Petal color*.—Pale pink [7. p.Pk] throughout on both sides.
*Stamen position*.—Typically located about 1/32" [0.8 mm] below the petals.
*Anther color*.—Moderate reddish orange [37. m.rO] over a Light yellow [86. l.Y] center at bloom onset.
*Pollen*.—Anthers produce an abundance of Brilliant yellow [83. brill.Y] pollen.
*Stigma color*.—Light greenish yellow [101. l.gY].
*Stigma position*.—Typically located about even with the nearby anthers.
*Ovary*.—Pubescent.
*Sepal color*.—Dark purplish red [259. d.pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—¼" [6.4 mm.].
*Sepal width*.—7/32" [5.6 mm.].
*Sepal apex*.—Rounded to elliptical to match the sepal length and width.
*Sepal margin*.—Fairly smooth.
*Sepal outer surface*.—Pubescent.
*Average pistil length*.—⅝" [15.9 mm.].
*Average stamen length*.—½" [12.7 mm.].
*Fragrance*.—Moderate.
*Blooming period*.—Early to medium, blooms two days after 'Snow Princess' (U.S. Plant Pat. No. 12,570) peach.
*Onset of bloom*.—One percent on Feb. 8, 2014.
*Date of full bloom*.—Feb. 15, 2014.
*Duration of bloom*.—One to two weeks, dependent on ambient temperature.
*Number per cluster*.—1 to 3 with single flowers most common.

FRUIT

Maturity when described: Firm ripe, Jun. 24, 2014.
Date of first picking: Jun. 20, 2014.
Date of last picking: Jun. 29, 2014.
Size: Uniform, large.
*Average diameter axially*.—3 3/16" [81.0 mm.].
*Average diameter across suture plane*.—3⅜" [85.7 mm.].
*Average diameter across cheek plane*.—3⅜" [85.7 mm.].
*Typical weight*.—12.0 ounces [340 grams].
Form: Uniform, globose to somewhat oblate, compressed axially, slightly asymmetrical.
*Longitudinal section form*.—Round to somewhat oblate.
*Axial view*.—Elliptical to round.
Suture: An inconspicuous line located in a very shallow groove extending from the base to just beyond the pistil point.
*Near the base*.—A shallow groove.
*Along the side*.—Protruding on one side with no groove.
*Near the apex*.—A shallow groove.
Ventral surface: Rounded with a slight breast on some.
Lips: Lipped on one side along the ventral surface and equally on both sides near the apex.
Cavity: Flaring, slightly elongated in the suture plane, suture showing on one side, Pale yellow [89. p.Y] stem markings typical.
*Depth*.—⅝" [15.9 mm.].
*Breadth*.—1⅛" [28.6 mm.].
Base: Somewhat truncate and slightly oblique.
Apex: Rounded to slightly truncate, somewhat cordate if viewed parallel to suture.
Pistil point: Oblique, negligible in length, usually depressed within the suture.
Stem: Medium.
*Average length*.—⅜" [9.5 mm.].
*Average width*.—3/16" [4.8 mm.].
Skin:
*Thickness*.—Medium.
*Surface*.—Pubescent.
*Down*.—Short, does not roll up when rubbed.
*Tenacity*.—Tenacious to flesh.
*Astringency*.—Non-astringent.
*Tendency to crack*.—None observed in dry season.
*Color*.—Dark red [16. d.R] over a Strong red [12. s.R] background.
Flesh:
*Color*.—Pinkish white [9. pkWhite] acquiring some Moderate red [15. m.R] streaking toward stone and Moderate red [15. m.R] flecking throughout with increased maturity.
Surface of pit cavity.—Covered with Light yellowish pink [28. l.yPk] fibers.
*Amygdalin*.—Scarce.
*Juice*.—Moderate, rich.
*Texture*.—Genetically melting, but remains firm and crisp through the harvest period.
*Fibers*.—Few, fine, tender.
*Ripens*.—Fairly even, slightly earliest at apex.
*Flavor*.—A tasty balance of acid and sugar, typically 16 to 18 brix.
*Aroma*.—Slight.
*Eating quality*.—Very good.

STONE

Type: Freestone.
Form: Oval.
Hilum: Narrow.
Base: Obtuse.
Apex: Acute, with a 1/16" [1.6 mm.] tip length.
Sides: Equal.
Surface: Irregularly furrowed toward the apex, pitted toward the base.
Ridges: Rounded.
External color: Dark yellowish brown [78. d.yBr].
Pit wall color when cracked: Moderate yellowish brown [77. m.yBr].

Cavity surface color: Strong yellowish brown [74. s.yBr].
Average pit wall thickness: ¼" [6.4 mm.].
Average width: 1" [25.4 mm.].
Average length: 1¼" [31.0 mm.].
Average breadth: ¾" [19.1 mm.].
Tendency to split: None observed.
Kernel:

*Form*.—Oval.
*Skin color*.—Pale yellow [89. p.Y] when first removed.
*Pellicle color*.—Light yellow [86. l.Y].
*Vein color*.—Brilliant yellow [83. brill.Y].
*Taste*.—Bitter.
*Viable*.—Yes.
*Average width*.—½" [12.7 mm ].
*Average length*.—⅝" [15.9 mm.].
*Amygdalin*.—Moderate.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'Pearl Princess V' (U.S. Plant Pat. No. 19,919) peach, by having a vigorous tree with large blossoms and reniform leaf glands, being self-fertile, and producing white flesh freestone peaches that are mostly red in skin color, globose to oblate in shape, firm in texture, and very good in flavor, but is distinguished therefrom by producing fruit that matures about seven days later and is somewhat larger in size.

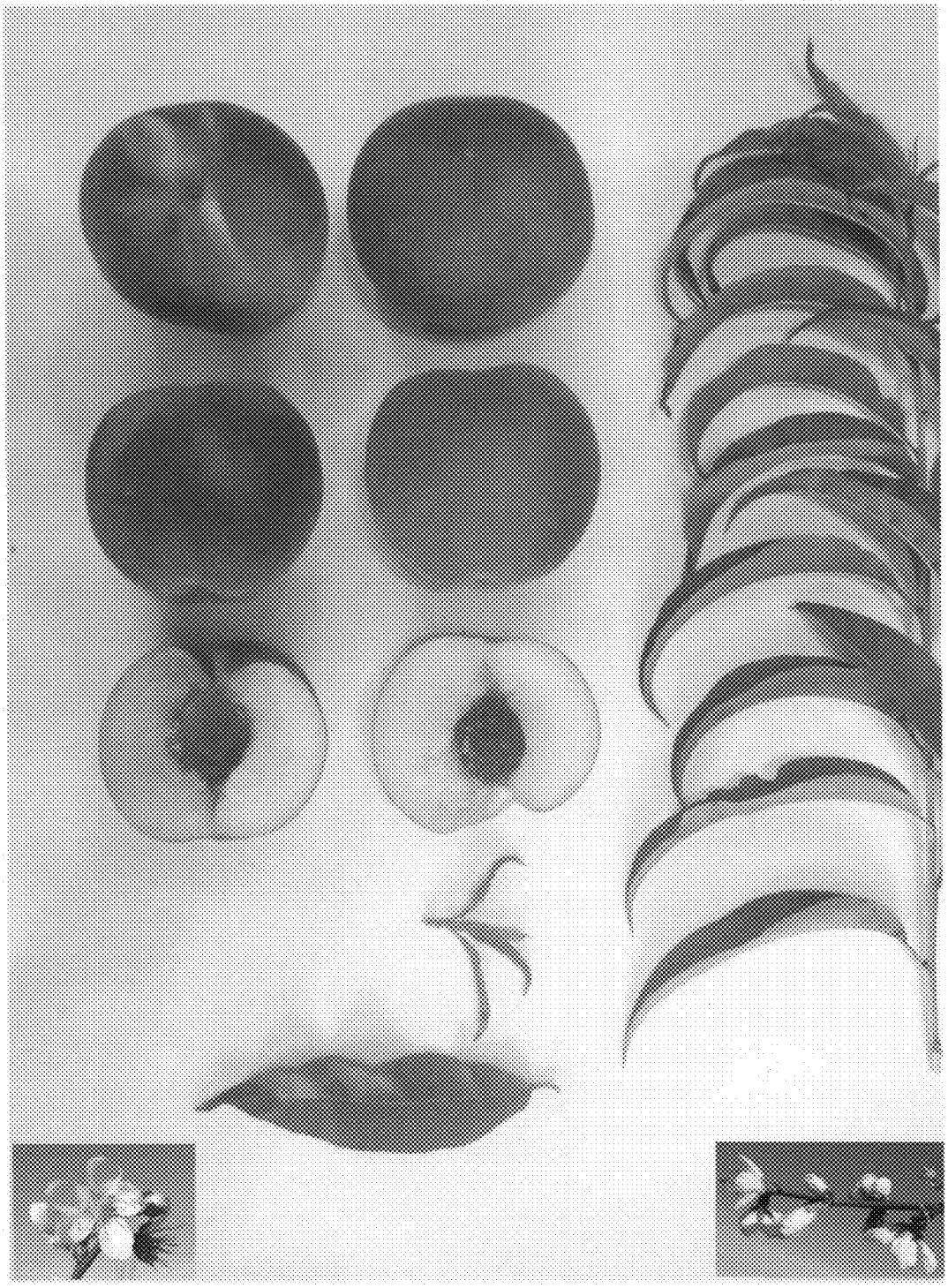

* * * * *